(12) United States Patent
Nanikashvili

(10) Patent No.: US 7,299,159 B2
(45) Date of Patent: Nov. 20, 2007

(54) HEALTH MONITOR SYSTEM AND METHOD FOR HEALTH MONITORING

(76) Inventor: Reuven Nanikashvili, 51/57 Atzmaut Street, Ashdod, 77452 (IL)

( * ) Notice: Subject to any disclaimer, the term of this patent is extended or adjusted under 35 U.S.C. 154(b) by 0 days.

(21) Appl. No.: 10/928,791

(22) Filed: Aug. 26, 2004

(65) Prior Publication Data

US 2005/0119833 A1    Jun. 2, 2005

Related U.S. Application Data

(63) Continuation-in-part of application No. 10/086,633, filed on Mar. 4, 2002, now Pat. No. 7,222,054, which is a continuation-in-part of application No. 09/261,136, filed on Mar. 3, 1999, now Pat. No. 6,366,871.

(60) Provisional application No. 60/076,660, filed on Mar. 3, 1999.

(51) Int. Cl.
*G06F 19/00* (2006.01)

(52) U.S. Cl. ........................ 702/188; 600/300

(58) Field of Classification Search ................ 702/188, 702/182–185; 600/300
See application file for complete search history.

(56) References Cited

U.S. PATENT DOCUMENTS

| | | | | |
|---|---|---|---|---|
| 5,853,005 | A * | 12/1998 | Scanlon | 600/459 |
| 6,083,248 | A * | 7/2000 | Thompson | 607/30 |
| 6,605,038 | B1 * | 8/2003 | Teller et al. | 600/300 |
| 6,616,613 | B1 * | 9/2003 | Goodman | 600/504 |
| 6,804,558 | B2 * | 10/2004 | Haller et al. | 607/30 |
| 2002/0124295 | A1* | 9/2002 | Fenwick et al. | 2/69 |
| 2004/0260156 | A1* | 12/2004 | David et al. | 600/300 |
| 2005/0124864 | A1* | 6/2005 | Mack et al. | 600/300 |

* cited by examiner

*Primary Examiner*—Edward Raymond
(74) *Attorney, Agent, or Firm*—Reches Patents; Oren Reches

(57) ABSTRACT

A mobile health monitor system that includes at least one physiological data sensor; at least one biomechanical data sensor; and a processing unit for correlating between physiological data and biophysical data. A method for health monitoring that includes: determining an occurrence of a measurement-initiating event; initiating an additional measurement in response to the occurrence of a measurement-initiating event; and correlating between gathered physiological data to provide correlated data.

19 Claims, 9 Drawing Sheets

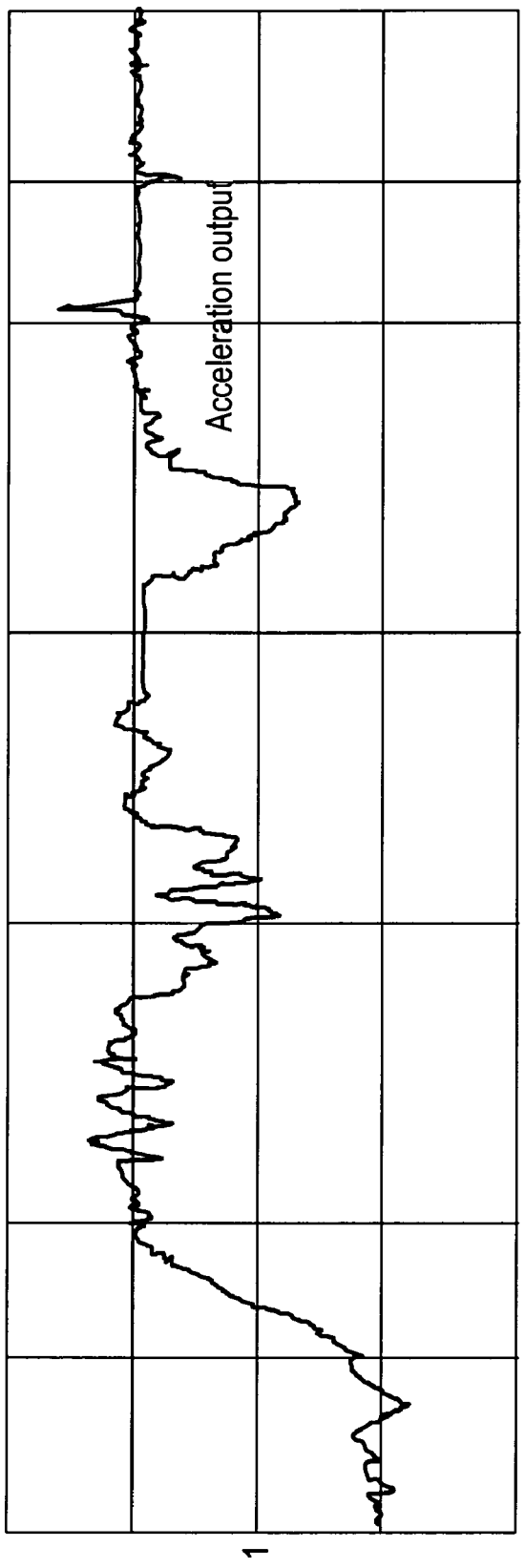
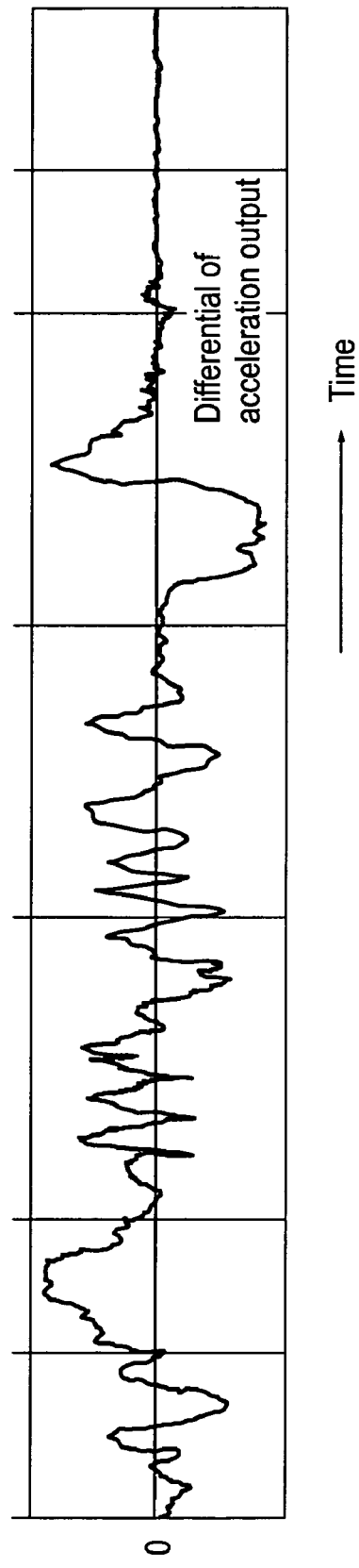
FIG. 6a
FIG. 6b

```
┌─────────────────────────────────────┐
│   determining an occurrence of      │
│   measurement initiating event.     │
│                              810    │
└─────────────────┬───────────────────┘
                  │
┌─────────────────┴───────────────────┐
│   performing an additional          │
│   measurement in response to the    │
│   occurrence of a                   │
│   measurement-initiating event      │
│                              820    │
└─────────────────┬───────────────────┘
                  │
┌─────────────────┴───────────────────┐
│   correlating between multiple      │
│   measured physiological data to    │
│   determine that a health related   │
│   event has occurred and/ or to     │
│   determine a health condition of   │
│   a person                          │
│                              830    │
└─────────────────────────────────────┘
```

HEALTH MONITOR SYSTEM AND METHOD FOR HEALTH MONITORING

RELATED APPLICATIONS

This patent application is a continuation in part of U.S. patent application Ser. No. 10/086,633 filed on Mar. 4, 2002 now U.S. Pat. No. 7,222,054 which is continuation in part of U.S. patent application Ser. No. 09/261,136 filed on Mar. 3, 1999, now U.S. Pat. No. 6,366,871, which claimed priority from U.S. provisional patent application Ser. No. 60/076,660 filed on Mar. 3, 1999.

FIELD OF THE INVENTION

The present invention relates to the field of biomedical monitoring devices. More specifically, the invention describes a multiple-input portable monitor.

BACKGROUND OF THE INVENTION

There are various types of physiological data types that can reflect the health of a person. Various physiological monitors are known in the art and include an electrocardiograph (ECG) monitoring device, a device for monitoring blood oxygen saturation, a device for monitoring respiration, a device for monitoring blood glucose, a device for monitoring blood pressure, a device for monitoring lung function, a device for monitoring SpO2 saturation, a device for monitoring temperature, a device for fat analysis, a fetal hart rate monitor device for pregnancy women, EEG device and the like. Each physiological monitoring device includes at least one sensor and may also include an analog component such as an analog amplifier, an analog comparator, an analog to digital converter and the like.

Physiological data of various types are responsive to the physical activity (or lack of such activity) of a person. For example, a person's blood pressure and heart beam can rise when that person is physically active. Yet another example, blood pressure is measured by a hand-mounted cuff and the physical status of that hand can affect the measurement.

Furthermore, correlation between physiological data of various types can provide vital information about various monitored events.

There is a need to provide a system and method for correlating between physiological data and physical activity of a person.

There is a further need to correlate between physiological data of various types.

SUMMARY OF THE INVENTION

The invention provides a method and system for correlating between biophysical data (data relating to a person's physiological activity) and between physiological data such as but not limited to, blood pressure, heart rate, ECG, breathing rate, and the like.

The invention provides a mobile health monitor system that includes at least one physiological data sensor, at least one biomechanical data sensor, and a processing unit. The processing unit is connected to the sensors, and is adapted to correlate between gathered physiological data and gathered biophysical data. These connections can include wires, wireless links and the like. Conveniently, the processing unit includes software and/or hardware components.

The invention provides a system and method for correlating between physiological data of various types, and especially for initiating at least one physiological data measurement when another physiological data measurement indicates that a measurement-initiating event occurs.

The invention provides a system and method for synchronizing between measurements of physiological data measurements of multiple types.

The invention further provides a system and method for wirelessly transmitting the multiple physiological measurements and/or physical activity related data from a person.

The invention provides a hand-mounted device that is capable of measuring at least one physiological data type and wirelessly transmit said data.

BRIEF DESCRIPTION OF THE DRAWINGS

For a better understanding of the present invention, reference is made to the accompanying drawings, which are incorporated herein by reference in which:

FIG. 6 shows an acceleration signal and the differential of acceleration signal, according to an embodiment of the present invention;

FIG. 7 is a flow chart of a method for health monitoring, according to an embodiment of the invention;

DETAILED DESCRIPTION OF THE DRAWINGS

Figure 1A:
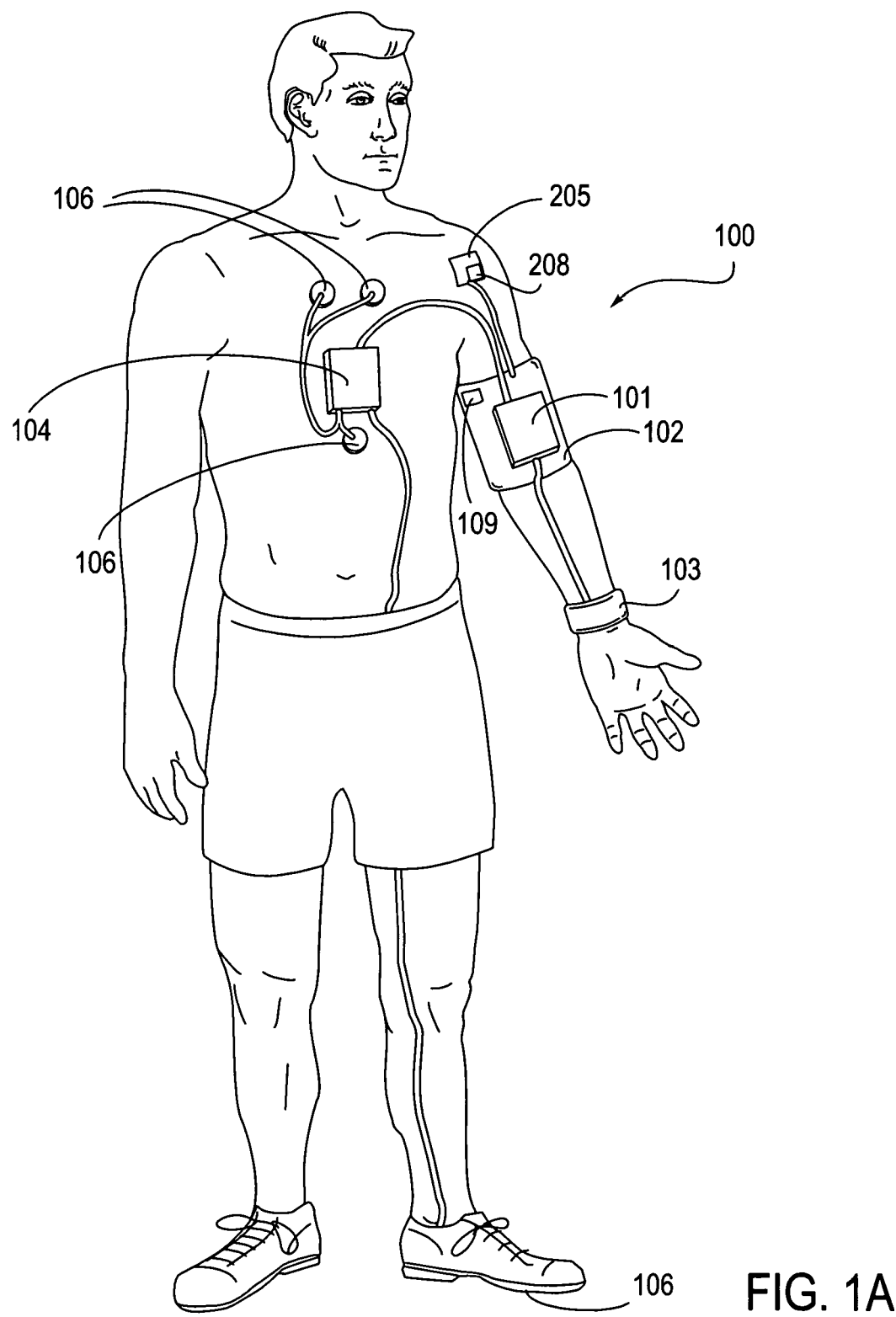
FIG. 1a depicts an embodiment of a monitoring device according to an embodiment of the present invention.

In the following detailed description, numerous specific details are set forth in order to provide a thorough understanding of the invention. However it will be understood by those of ordinary skill in the art that the present invention may be practiced without these specific details. In other instances, well-known methods and procedures have not been described in detail so as not to obscure the present invention.

The term sensor refers to a sensor but also refers to analog and/or digital circuitry that is required for at least initially processing the sensor output before being transmitter and/or processed by a processing unit.

In one embodiment of the device, system and method of the present invention, a typically portable monitor (e.g., a Holter monitor, although other types of monitors may be used), collects physiological data from a person, typically in real time using a variety of sensors. U.S. Pat. No. 6,366,871 of Geva describes a multiple input monitor.

Typically collected are one or more items of physiological data (such as heart rate, ECG, blood pressure, breathing rate and others), and, simultaneously, data relating to physical activity (also referred to as biophysical data), such as, for example, movement, body attitude and musculoskeletal loading. Such monitoring may occur during daily activity, outside of a doctor's office. The collected data can be, for example, recorded and/or downloaded to or transmitted to a computer, cellular phone, personal data accessory and the like for analysis.

Physiological data correlated with person physical activity data may be useful for, for example, assessment of cardiovascular health and risk factors associated with habitual patterns of daily activity. Embodiments of the present invention may allow the collection of physiological data that is associated with simultaneous body movements of a person, along with data on such body movements.

The collected physiological data as well as data relating to the person activity can be wirelessly transmitted to short range transceivers that in turn relay the information or otherwise provide the information to long range transceiver systems such that the data eventually is sent to remote locations including remote data bases, remote medical centers and the like. Various short-range transmission standards such as but not limited to Bluetooth, WLAN, ZigB, Wi-Fi, WLAN, UWB, and the like.

The long-range transmission can be executed at real time but this is not necessarily so. Various long-range transmission networks can be utilized, such as but not limited to, LAN, Cable TV, Satellite TV, CCTV, Telephone line, GSM/GPRS, CDMA, TDMA, iTV, Internet and the like.

The health monitor system can exchange data with a long-range transceiver such as a cellular phone, a personal data accessory PDA, and the like.

The physiological data as well as the physical activity related data can be processed by the monitor or the long-range transceiver. U.S. patent application titled "Personal health monitor and a method for health monitoring" which is incorporated herein by reference and illustrates a transceiver that also processes physiological data before transmitting it.

The health monitor system can include one or more physiological data sensor, physical activity sensor, a processor and a transceiver. These elements can be connected by wire or by wireless communication.

FIG. 1a depicts a health monitoring system according to an embodiment of the present invention. Referring to FIG. 1a, health monitoring system 100 includes a processing unit 101 which may be attached to, for example, a person's upper arm. Typically, processing unit 101 is of similar construction and operation to a lightweight Holter type device, with certain modifications according to embodiments of the invention, but may be of other configurations.

The air pressure arm cuff could be the blood pressure arm cuff. By attaching the processing unit 101 to The Blood pressure arm cuff 102 a very efficient health monitor system is provided. This system can even include an integration of a processing unit 101 to additional sensors that are connected to the blood pressure arm cuff 102, thus providing a health monitor system that can be worn or removed very quickly, and does not require wires of wireless connections between a processing unit and sensors, thus reducing the cost of such a system, increasing its reliability and making it more easy to wear. This blood pressure upper arm cuff device could be also blood pressure holter for 24 hours or more. This device could be programmed via processing unit 101, via Personal computer, Cellular phone or PDA.

Processing unit 101 may be mounted on or otherwise attached to other sensors, transceivers or devices and can be embedded within other devices. The processing unit 101 is connected, to one or more physiological data sensors. Conveniently, the processing unit 101 can be attached to an air pressure arm cuff 102, which provides typically automatic measuring of blood pressure values. In one embodiment, air pressure arm cuff 102 includes pressure sensor 109, measuring the air pressure in the arm cuff 102. Additional physiological data may be corrected. Typically, processing unit 101 stores, inter alia, a series of blood pressure values signed by time; other data formats may be used and other data may be stored. Processing unit 101 need not be attached to pressure cuff 102.

Processing unit 101 may be connected to, for example, at least one biophysical data sensor such as accelerometer sensor 103, typically attached to the person's wrist or lower arm, an attitude sensor 104, typically attached to the person's chest or torso, and a foot step or ground contact sensor 105, typically located at a persons foot, typically on the insole. These biophysical data sensors provide an indication about physical activity of the person.

In alternate embodiments, other sets of sensors and types of sensors may be used, and the sensors may be placed in other locations. Typically, the various units are connected by suitable wires, cables carrying electric signals, or by utilizing wireless links.

The accelerometer sensor 103 may be used (when placed on one position on the person's body) as a hand motion sensor, detecting particular hand moving patterns. The attitude sensor 104 may provide attitude sensing, measuring acceleration or other physical properties of the person's body (e.g., position, orientation) in, typically, three orthogonal axes. Data produced by attitude sensor 104 may allow for calculation or determination of the person's body attitude, position, or orientation, for example relative to vertical axis. In one embodiment, the foot step sensor 105 includes a strain gage sensing insole placed into the person's shoe, used to monitor the pressure of the foot; other configurations are possible.

Figure 1B:
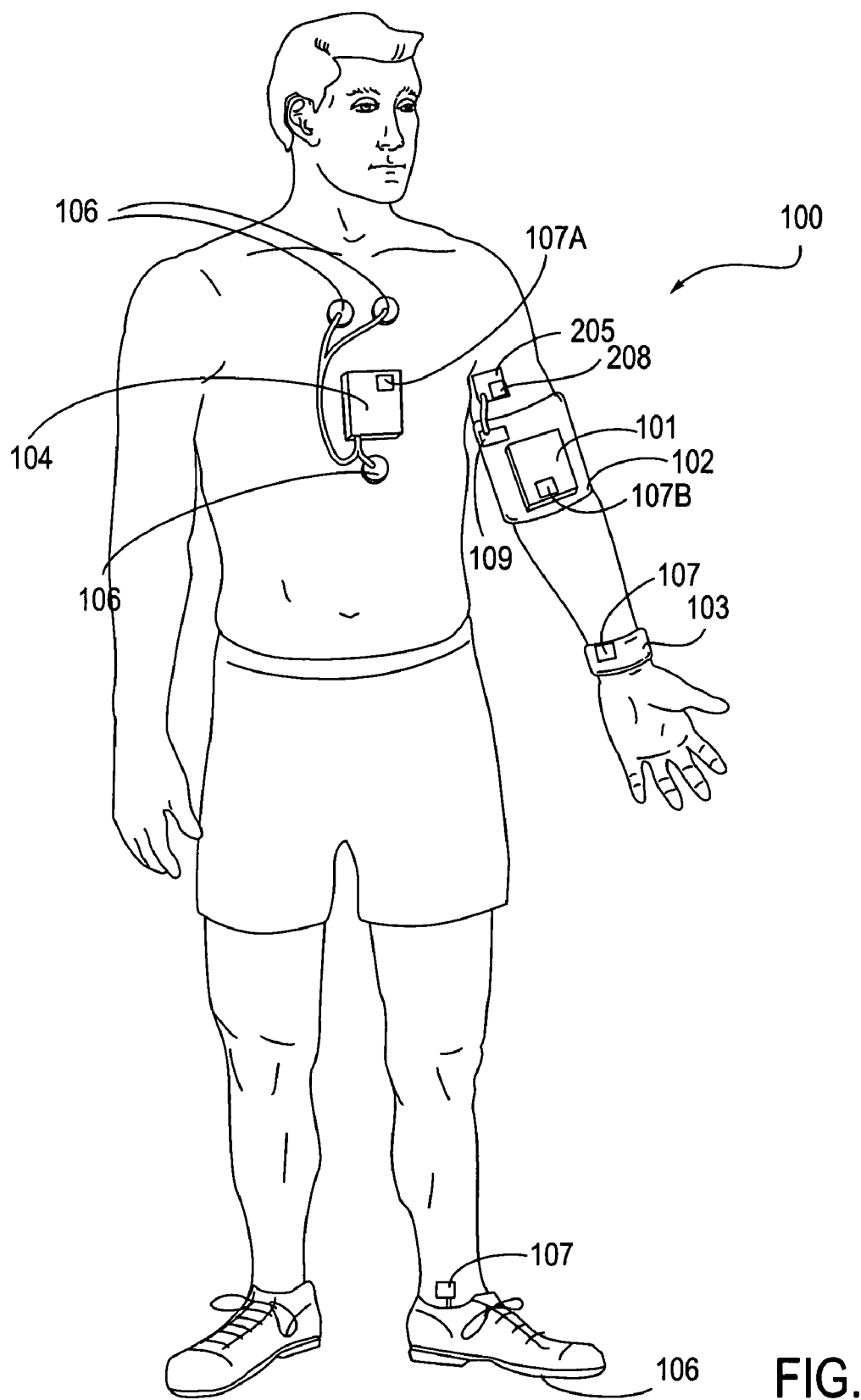
FIG. 1b depicts an embodiment of a monitoring device according to an embodiment of the present invention.

FIG. 1B depicts a monitoring system using bi-directional wireless connections according to an embodiment of the present invention. Referring to FIG. 1B, system 100 includes, for example, a processing unit 101, an arm cuff 102, an accelerometer sensor 103, an attitude sensor 104, a ground contact sensor 105, and electrodes 106 attached to the person chest. Certain of the units 101, 102, 103, 104, 105 and possibly 106 may be connected using a wireless connection. In one embodiment, each of units 103, 104 and 105 include a transmitter 107a, which typically uses known Bluetooth™ standard technology to transmit the data output by such units to a receiver 107b, located in processing unit 101. Typically, since processing unit 101 is mounted on or adjacent to arm cuff 102, units 101 and 102 need not communicate wirelessly. If processing unit 101 and arm cuff 102 are otherwise located, data may be communicated between them wirelessly. Receiver 107b typically uses known Bluetooth™ standard technology to receive data output by the various physiological monitoring units.

The wireless connections can be utilized for conveying instructions to initiate a measurement when one of the sensors detected that an event occurs (for example raise of blood pressure or heart rate above a certain threshold), or in a periodical manner.

Synchronization between multiple measurements can provide vital information to the person or to a doctor. By analyzing physiological data gathered from various sensors the monitoring system can determine if an event occurred, if there is a need to ask person to initiate additional measurements and/or if to transmit the data to a remote system, whether to generate an alarm signal to the person, and the like. The alarm signal can also include a request to call a certain number (for example of a remote medical center, of a doctor and the like), and can also instruct the person to perform certain acts (for example- to rest, drink, take a drug and the like).

Figure 2:
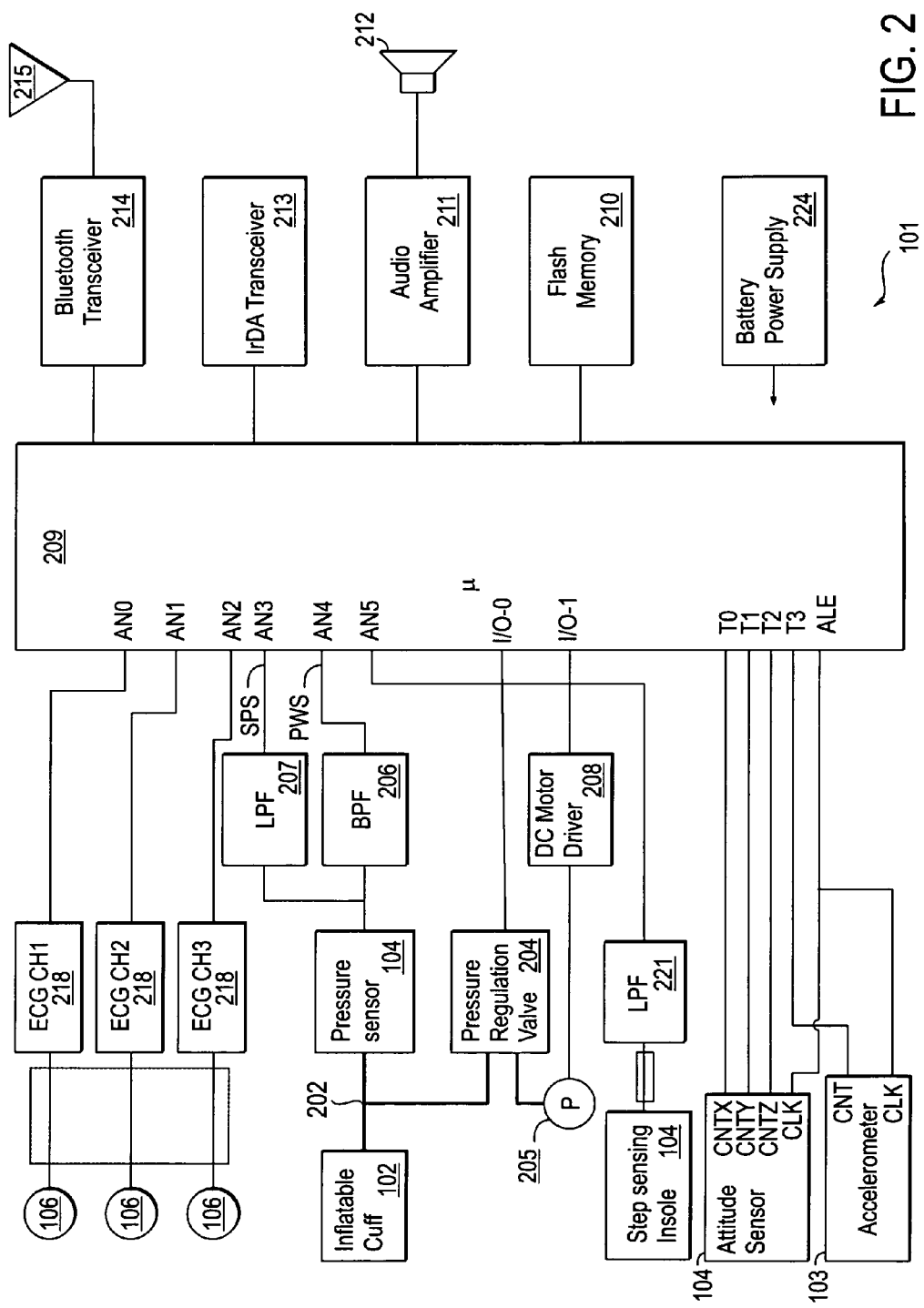
FIG. 2 is a block diagram of electric arrangement of the Holter, according to an embodiment of the present invention.

FIG. 2 is a block diagram of various components of the monitoring system 100, according to one embodiment of the present invention. Referring to FIG. 2, an inflatable arm cuff 102 is connected via tubing or piping 202 to a pressure sensor 109, a cuff-pressure regulator valve 204, and an air pump 205. Other known devices and systems for blood pressure monitoring may be used, having different configuration and functionality. In the system depicted in FIG. 2, data may be transferred wirelessly, in one embodiment using the Bluetooth™ standard. In alternate embodiments, other wireless standards and equipment may be used.

The processing unit 101 includes a band-pass filter 206, a processor such as micro-controller 209, a low-pass filter 207, a low pass filter 221, and one or more ECG amplifiers 218. The micro-controller 209 typically includes a built-in A/D converter (not shown), a read only memory (ROM, not shown) and random access memory (RAM, not shown).

In alternate embodiments such components may be external to the micro-controller 209. The micro-controller 209 may communicate with other devices such as a memory (typically a flash memory) 210, audio amplifier 211, speaker 212, for transmission via phone network (e.g., PSTN), infrared (IR) transceiver 213, a wireless transceiver 214 using, for example the Bluetooth™ standard, and an antenna 215. Other sets of components and other combinations of components may be used. The micro-controller 209 typically processes input signals according to, for example, the control programs stored in a ROM or other memory contained within or connected to micro-controller 209 by, for example, utilizing the temporary-storage function of the RAM, and may produce a drive or control signal to control components of the processing unit 101 to, for example, perform tests. Processing unit 101 may, for example, be connected to a motor 208 and valve 204 for controlling cuff 102. The battery power supply 224 supplies required voltages for components of the processing unit 101. Storage methods other than a flash memory may be used.

On receipt by processing unit 101, the output signal of the pressure sensor 109 (and possibly other received signals) may be processed locally, in processing unit 101. Alternately, such signals may be processed on a remote device, for example at a doctor's office. For example, the of the pressure sensor 109 signal may be input to band-pass filter 206, which selectively transmits a heartbeat-synchronous oscillatory component of the received pressure signal as a pulse wave signal, "PWS," to an analog input AN4 of micro-controller 209. The pulse wave signal PWS typically represents the pulse wave produced from the pressed arteries of the subject's arm, propagated to the inflatable arm cuff 102 providing pressure on the arm. The pressure signal of the pressure sensor 109 may also be input to, for example, a low-pass filter 207, which may selectively transmit a static component of the received signal, as a cuff pressure signal, "SPS," to the analog input AN3 of micro-controller 209. In one embodiment, the cuff pressure signal SPS represents the change of static pressure within the inflatable arm cuff 102. Other methods and devices for processing the output of the pressure sensor may be used, and, in alternate embodiments no processing need be performed by the local unit worn on the person.

To measure blood pressure, the micro-controller 209 may, for example, send drive signals to the motor driver 208 of air pump 205 to inflate the cuff 102 and thereby press the upper arm, and may feed drive signals to the cuff-pressure regulator valve 204 to gradually reduce the cuff pressure of the cuff 102. The micro-controller 209 receives, during the reduction of the cuff pressure, the pulse wave signal PWS and the cuff pressure signal "CPS" from the pressure sensor 109 via the respective filters 206, 207. The micro-controller 209 determines, based on the received signals PWS and CPS, the systolic (SAP) and diastolic (DAP) blood pressure values of the subject [Inventor: the following isn't clear—do you mean "using" instead of "in"?] in the known oscillometric blood pressure measuring process, respectively. The micro-controller 209 collects the SAP and DAP values in, for example, a blood-pressure (BP) memory areas of a flesh memory 210. In one embodiment, the arm cuff 102, air pump 205, pressure sensor 109, filters 206 and 207, and micro-controller 209 cooperate with each other to provide a blood pressure Holter.

Processing unit 101 can at the same time function as, for example, an ECG three-channel Holter. ECG signals capture by electrodes 106 may be input to the ECG amplifiers 218. Analog ECG signals from the amplifiers 218 are transferred to the analog inputs of the built-in A/D converter of the micro-controller 209. Samples of the ECG signal may be collected in the flesh memory 209. Other numbers of signals, other sets of signals, and other types of signals, may be captured.

The processing unit 101 can be connected to additional sensors, such as but not limited to those described in U.S. Pat. No. 6,366,871 of Geva. According to an embodiment of the micro-controller 209 is capable of receiving inputs from one or more physiological sensor and in response initiate a measurement of another physiological sensor. Micro-controller 209 can also initiate multiple measurements according to a predefined schedule.

According to an embodiment of the invention if a certain measurement requires human intervention, the processing unit 101 can generate a vocal request to the person to assist in said measurement.

Figure 3A:
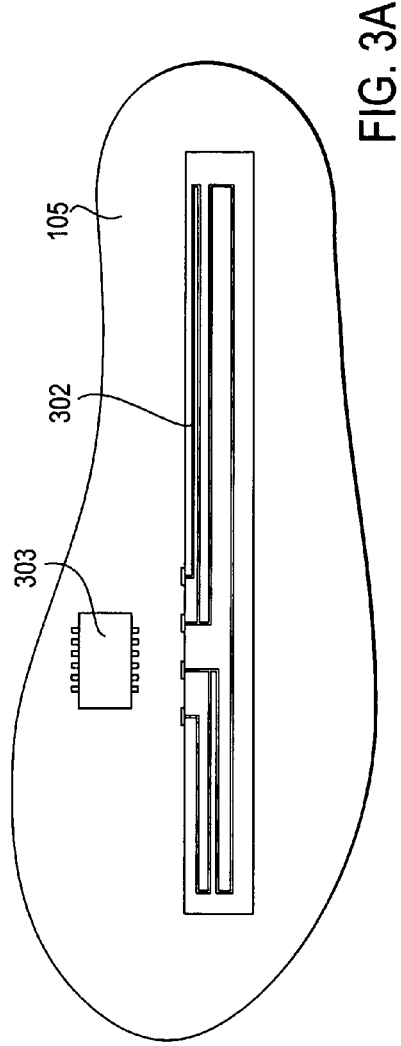
FIG. 3 presents a construction diagram of the of sensing insole, according to an embodiment of the present invention.
Figure 3B:
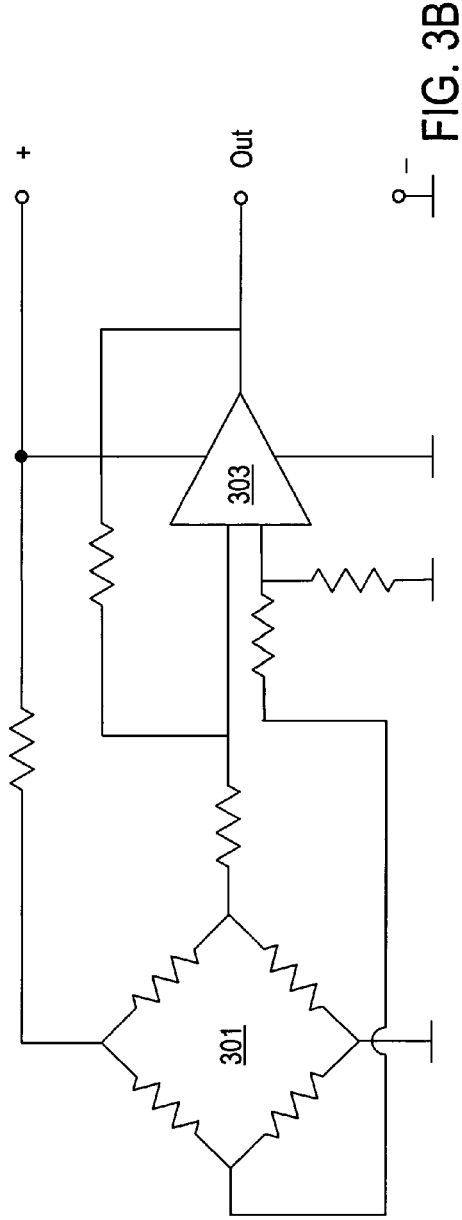

Data from foot step sensor 105 (which is typically placed in a person's shoe) may be used, for example, for monitoring a person's daily activity. FIGS. 3a and 3b illustrate two embodiments of possible construction of foot step sensor 105. Other embodiments are possible. Other types of foot or step sensors may be used, not placed inside a shoe or on the foot.

Referring to FIG. 3a, foot step sensor 105 includes, for example, strain gage transducer 302 and temperature compensated amplifier 303. The output voltage of amplifier 303 is transferred via a suitable connecting cable through low pass filter 221 (FIG. 2) to the analog input of the built-in A/D converter of micro-controller 209. The input data may be, for example, processed by a digital signal processing program in real time.

FIG. 3a depicts a foot step sensor using wireless communication with processing unit 101. For example, Bluetooth™ standard wireless technology may be used. The output signal of the foot step sensor may be transferred through low pass filter 221 (FIG. 2) to the analog input of the built-in A/D converter of micro-controller 209. The input data may be, for example, processed by digital signal processing program in real time and transmitted via, for example, a wireless modem to the processing unit 101.

Certain embodiments of the invention may include a system and method for activity measurement such as that described in U.S. Pat. No. 6,183,425 to Whalen and Breit, incorporated herein by reference. The 6,183,425 patent describes, inter alia, a system and method for quantifying daily activity in terms of daily history of the vertical component of the ground reaction force (GRFz). The device includes a sensor placed in a shoe which detects the contact of the foot with the ground. The time of occurrence of each significant foot-down and foot-up event may be recorded. Ground contact time may be identified as, for example, walking, running or "special" by the value of the contact-time interval and may reject a contact pair that falls outside of the known walking or running contact time to stride period relationship. The timing events may be, for example, converted to cyclic peaks of GRFz using appropriate walking and running regression equations. The system and method provide an "activity index," reflecting walking and running energy consumption. An embodiment of the present invention may use such methods to quantify the person body activity during normal daily activity.

The data received from the sensing insole 105 is typically processed by a digital signal processing program, typically controlled by micro-controller 209.

During processing, noise and spurious non-significant contacts, like foot tapping or not true gait cycles may be reduced. The signal may be compared to the high and low levels values to capture the primarily weight-bearing contacts. The times of foot contact to ground in pairs of foot-down and foot-up events may be collected sequentially, with other data, in memory 210. This raw data of the periods of contact cycles may be, for example, downloaded to a local computer or transferred to the remote station for farther processing.

Figure 4:
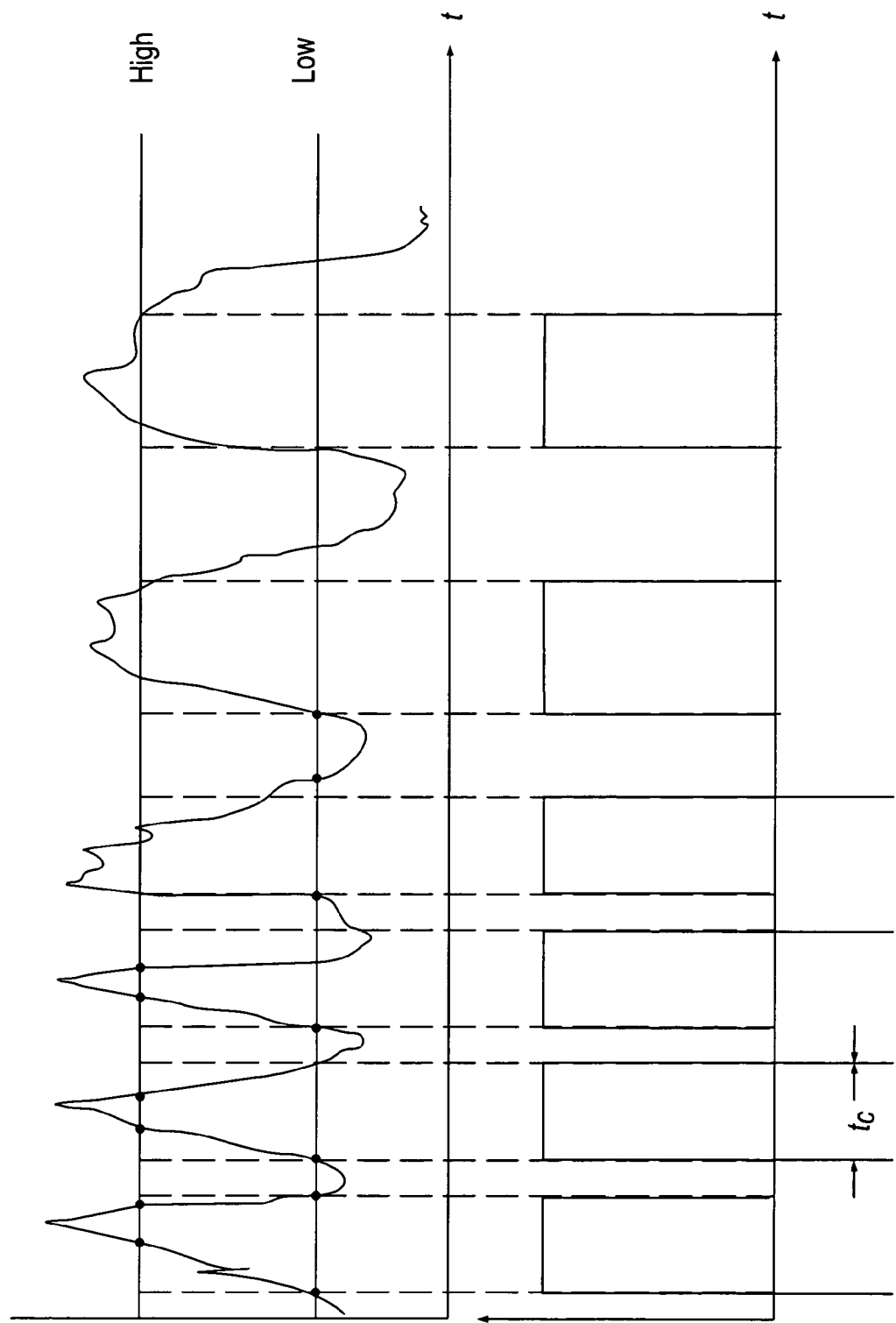
FIG. 4 illustrates the algorithm for detection a contact period $t_c$, according to an embodiment of the present invention.

In one embodiment, the duration of the pulse at the output of the amplifier 221, or the minimum foot ground contact time during running which indicates a foot fall may be, for example, about 0.15 sec. Using a sampling rate of 250 samples per second (or 4 msec duration between samples), about minimum 37 samples per single pulse or foot fall is obtained. FIG. 4 illustrates the input and output data for a sample contact period $t_c$ detection algorithm using the high and low threshold values crossing technique. Other specific values may be used, and other algorithms or processing techniques may be used.

The attitude sensor 104 may be implemented using, for example a Triaxial Digital Accelerometer Model 2420 from Silicon Designs, Inc. The Model 2420 contains three orthogonally mounted Model 1010 integrated accelerometers. The module produces three pulse train outputs. The outputs of the sensor 104 may be connected to the counter inputs T0, T1, T2 of the micro-controller 209 (FIG. 2).

Figure 5:
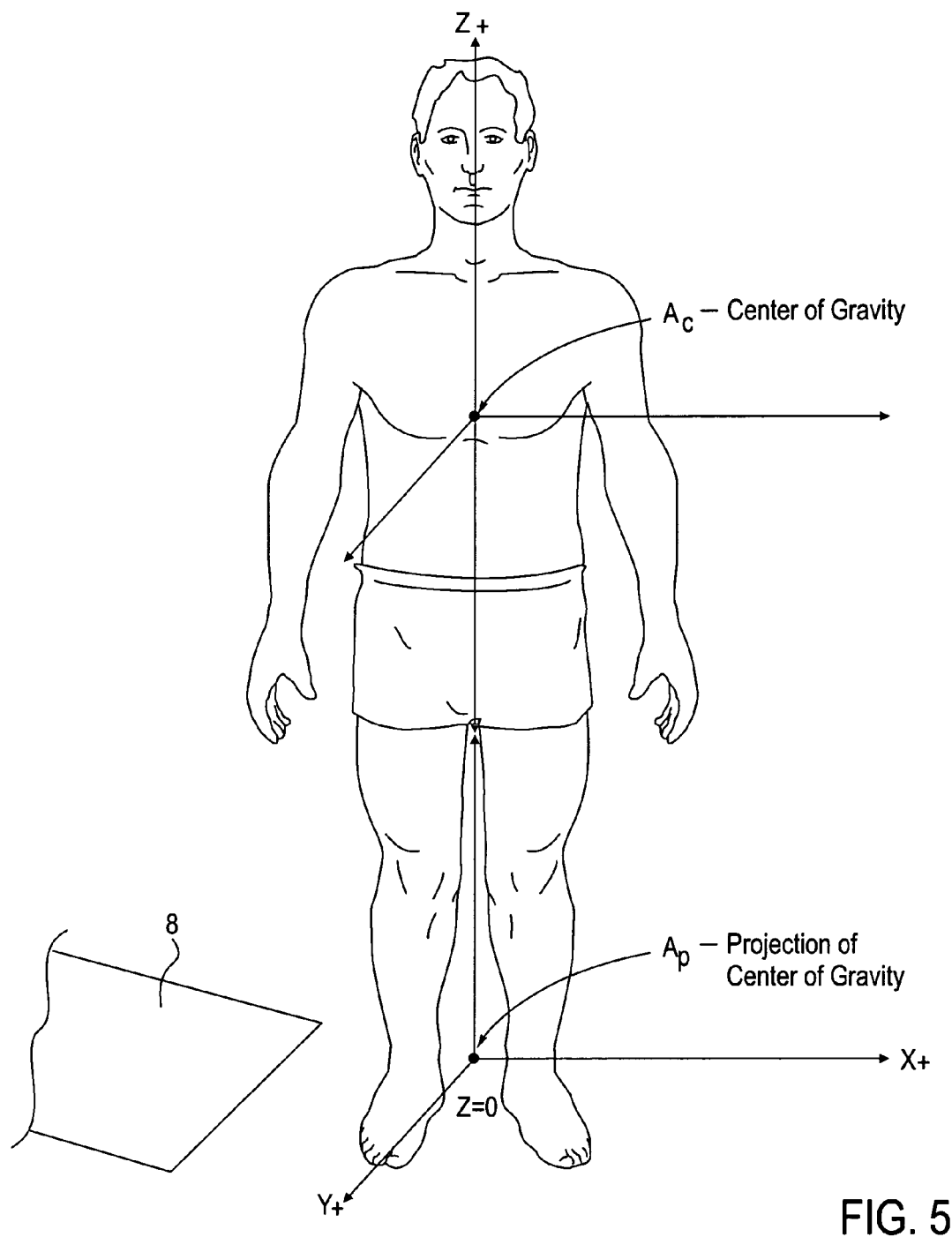
FIG. 5 is shown a coordinate set of axes X, Y and Z that designate person's body, according to an embodiment of the present invention.

Referring now to FIG. 5 there is shown a coordinate set of axes X, Y and Z designating a person's body orientation with respect to the 'horizon' 8 as reference plane, according to one embodiment of the present invention. Rotation motions may be defined within these planes and around these axes, such as 'pitch' (rotation about Y in XZ plane), 'roll' (rotation about X in YZ plane) and 'yaw' rotation about Z in XY plane). Triaxial acceleration monitoring using, for example, attitude sensor 104, may be used to provide a calculation of the center of gravity $A_c$ orientation relative to the projection of this center $A_p$ on the XY plane at a vertical position of the body and coordinate Z=0. The deviation of the person's body from a vertical position causes the changes of the output signals of the sensor 104. These signals may be sampled and, for example, stored in the memory 210 signed by the time for synchronizing with other simultaneously monitored parameters. Further processing of the stored data may provide detection of the person body orientation (e.g., rest, moving in a horizontal plane, moving in vertical plane, rapid or incidence fall, etc.). This information, in correlation with heart rate, blood pressure and other parameters may be used to perform a person health condition analysis during person daily exercising.

The accelerometer sensor 103 may include, for example, a digital accelerometer Model 1010 from Silicon Designs, Inc. Accelerometer sensor 103 may be used for, for example, monitoring the motions of the person hand to which the inflatable arm cuff 102 is attached. Such an accelerometer may be attached at another body position, such as on the leg. The Model 1010 accelerometer produces a pulse train in which the density of pulses (number of pulses per second) is proportional to the applied acceleration. It combines in a single, miniature, hermetically sealed package a micromachined capacitive sense element and an integrated circuit that includes, for example, a sense amplifier and a sigma-delta A/D converter. It is relatively insensitive to temperature changes and gradients. The output signal of the accelerometer sensor 103 may be connected to, for example, the counter input T1 of the micro-controller 209 (FIG. 2). The data of the signal samples may be, for example, stored in the memory 210 signed by time for synchronizing with other simultaneously monitored data. Further analysis of the data downloaded to the computer may provide elimination of the spurious results of, for example, a blood pressure measurement caused by a hand moving during the measuring process. Other accelerometers or methods and systems of measuring acceleration or body movement may be used.

FIG. 6a depicts a sample acceleration signal produced by processing data received from sensor 103, according to an embodiment of the present invention. This acceleration signal shows changes of velocity of a person's movements. It includes oscillation and constant components. For detection of a hand's rapid movements this signal may be processed and, for example, a differential of acceleration may be calculated. FIG. 6b shows the differential of the acceleration depicted in FIG. 6a, according to one embodiment. The analysis of this signal may provides detection of, for example, the rapid or significant motions of the hand, such as components 601 and 602.

Typically, various physiologic, vital signs, physical and body orientation/activity data are collected substantially simultaneously and are recorded and/or transmitted to a remote site (e.g., a doctor's office) for analysis. Vital signs data may be analyzed in correlation with physical activity. The data collected may be, for example, time stamped, so that it can be displayed or analyzed side by side. For example, each data item may be signed by time for synchronizing with other simultaneously monitored data.

Data stored in the memory 210 can be, for example, downloaded to an external computer or workstation which may include, for example, the appropriate signal analyzing and display capabilities. Various methods of data transfer may be used, for example, a wireless link (such as using the Bluetooth™ standard or a defines an infrared method such as that defined by the IrDA standard), a modem link (such as via PSTN phone network through audio communication interface), or other methods.

In one embodiment, the wireless transceiver module 214 (FIG. 2) includes a hardware chipset which includes radio, baseband, LMP and L2CAP layers for the Bluetooth™ standard. The data from application layer is sent over the physical bus to the L2CAP layer of the wireless transceiver module 214. Data flows from micro-controller 209 through wireless transceiver module 214, through the physical radio layer to the antenna 215. In a typical embodiment data interchange between micro-controller 209 and the Bluetooth™ standard protocol stack is performing using a standard communication application.

In one embodiment, IR transceiver 213 (FIG. 2) uses the IrDA protocol, and includes transmission and receiver infrared diodes (not shown). The data interchange between micro-controller 209 and IR transceiver 213 may be performing using, for example, the same communication protocol that used to communicate with the wireless transceiver module 214.

Transmission to a local or remote computer or workstation via, for example, a PSTN phone network may be performed using, for example, Frequency Sift Key (FSK) technology for data transfer. The modulated by data carrier frequency signal may be generated by an audio software module (not shown) and the sequence of the pulse train is driven through the audio amplifier 211 (FIG. 2) to the audio transducer (or speaker) 212.

The memory 210 may be used for storage of collected parameters. In a typical embodiment memory 210 is included within the processing unit 101. In other embodiment memory 210 can be, for example, a removable mini flashcard that can be connected to a reader for downloading stored data to, for example, a local or remote computer for further processing and analysis.

FIG. 7 is a flow chart of method 800 of health monitoring, according to an embodiment of the invention.

Method 800 starts by stage 810 of determining an occurrence of measurement initiating event. According to an embodiment of the invention a measurement initiating event is responsive to a value obtained as a result of a measurement of physiological data. For example, once blood pressure exceeds a certain threshold the monitoring system can determine that a measurement initiating event occurred.

According to another embodiment of the invention the measurement initiating event can relate to certain time schedule but can also be responsive to a combination of a certain measurement result and certain timing schedule.

Stage 810 is followed by stage 820 of performing an additional measurement in response to the occurrence of a measurement-initiating event. Conveniently, if this additional measurement can be performed without intervention the monitoring system performs said measurement. Else, a request to initiate such a measurement is generated and in response the additional measurement can be at least partially manually executed.

It is noted that the additional measurement can include measuring a physiological parameter and/or measuring biophysical data.

Stage 820 is followed by stage 830 of correlating between multiple measured physiological data to determine that a health related event has occurred and/or to determine a health condition of a person. A health related event can be a cardiac event, an abnormal raise or decrease in blood pressure, an abnormal raise or decrease in heart rate, an abnormal raise or decrease in oxygen saturation in blood, an abnormal raise or decries in glucose level in blood, event from fall detector, events from EEG sensors (sleep and/or wake up duration), event from Spiro meter sensor and the like.

The correlation can be executed by one or more devices, including a monitoring system, a computer, a cellular phone, a personal data accessory, and/or a remote station. Accordingly, stage 830 can be preceded by or followed by transmitting and/or receiving data.

It is noted that an event or even a measurement initiating event can be defined in advance, either in relation to the person medical history or not.

Figure 8:
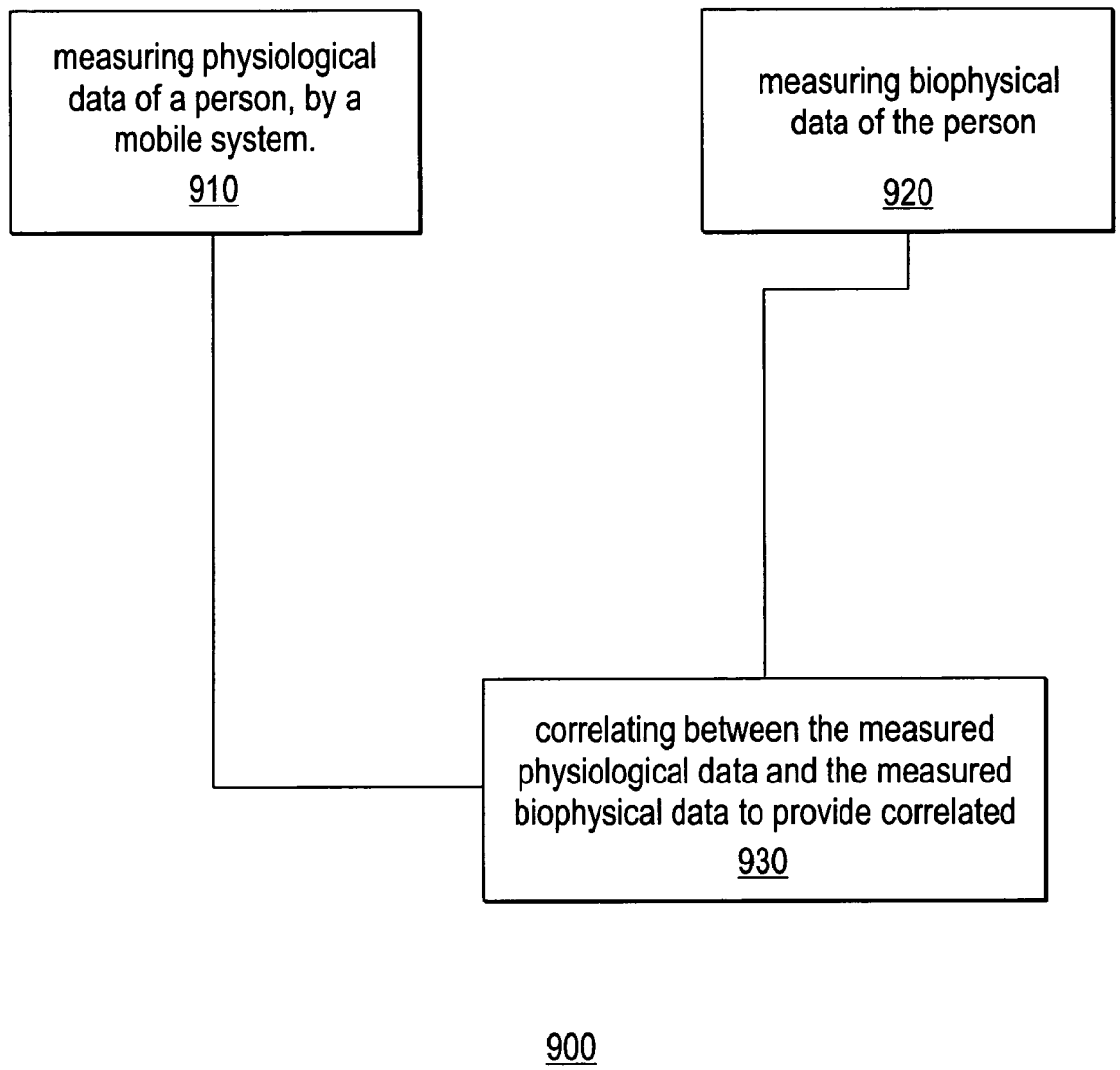
FIG. 8 is a flow chart of a method for health monitoring, according to another embodiment of the invention.

FIG. 8 is a flow chart of method 900 of health monitoring, according to an embodiment of the invention.

Method 900 starts by stages 910 and 920. Stage 910 includes measuring physiological data of a person, by a mobile system.

Stage 920 includes measuring biophysical data of the person.

Stages 910 and 920 are followed by stage 930 of correlating between the measured physiological data and the measured biophysical data to provide correlated data. The correlated data can be transmitted to a remote location, stored, processed, and the like. It can be analyzed for determining if a health related event occurred, to provide an indication about the health status of a person and the like.

It will be appreciated by those skilled in the art that while the invention has been described with respect to a limited number of embodiments, many variations, modifications and other applications of the invention may be made which are within the scope and spirit of the invention.

What is claimed is:

1. A health monitor system comprising: at least one physiological data sensor; at least one biomechanical data sensor configured to collect biophysical data relating to musculoskeletal loading; and a processing unit, coupled to the at least one physiological data sensor and to the at least one biomechanical data sensors, for correlating between physiological data and the biophysical data.

2. The health monitor system of claim 1 comprising a long-range transmitter, coupled to the processor.

3. The health monitor system of claim 1 integrated in a long-range transmitter.

4. The health monitor system of claim 3 wherein the long-range transmitter is a PDA or a mobile phone.

5. The health monitor system of claim 1 wherein the processing unit is integrated in a blood pressure device adapted to be mounted on an arm cuff.

6. The health monitor system of claim 1, whereas the system is adapted to provide physiological data reflecting heart function.

7. The health monitor system of claim 1, whereas the system is adapted to provide physiological data reflecting lung function.

8. The health monitor system of claim 1 wherein the processing unit is mounted on a hand cuff.

9. A mobile health monitor system comprising: multiple physiological data sensors adapted to gather physiological data of multiple types; at least one biomechanical sensor adapted to measure biomechanical data at least one biophysical data sensor configured to collect biophysical data relating to musculoskeletal loading and a processing unit, coupled to the multiple physiological data sensors, adapted to determine an occurrence of a measurement initiating event, to correlate between the physiological data and the biophysical data and to initiate an additional measurement of biomechanical data in response to the occurrence of a measurement-initiating event.

10. The health monitor system of claim 9 comprising a long-range transmitter, coupled to the processor.

11. The health monitor system of claim 9 further adapted to correlate between multiple physiological data and to determine an occurrence of a health related event.

12. A method of health monitoring, the method comprising: gathering physiological data, biophysical data related to musculoskeletal loading and biomechanical data; and correlating between the gathered physiological data, biomechanical data and biophysical data to provide correlated data.

13. The method of claim 12 further comprising long-range transmitting the correlated data.

14. The method of claim 12 whereas the physiological data reflects heart function.

15. The method of claim 12, whereas the physiological data reflects lung function.

16. The method of claim 12 further comprising a stage of providing a hand-mounted processor unit.

17. The method of claim 12, wherein the stage of gathering biomechanical data comprises gathering data on foot falls.

18. The method of claim 12, wherein the stage of gathering biomechanical data comprises gathering data on body attitude.

19. A health monitor system, comprising: a hand cuff; a biophysical data sensor configured to collect biophysical data relating to musculoskeletal loading and a processing unit, adapted to be coupled to at least one physiological data sensor, and coupled to the hand cuff, for processing physiological data and correlating between the physiological data and the biophysical data.

\* \* \* \* \*